United States Patent
Deal et al.

(10) Patent No.: US 9,205,162 B2
(45) Date of Patent: Dec. 8, 2015

(54) INSTRUMENT DISINFECTOR

(71) Applicant: UVAS, LLC, Charleston, SC (US)

(72) Inventors: Jeffery L. Deal, Charleston, SC (US);
David R. Deal, Sugar Hill, GA (US);
Philip J. Ufkes, Sullivans Island, SC (US)

(*) Notice: Subject to any disclaimer, the term of this patent is extended or adjusted under 35 U.S.C. 154(b) by 79 days.

(21) Appl. No.: 14/215,397

(22) Filed: Mar. 17, 2014

(65) Prior Publication Data

US 2014/0271348 A1    Sep. 18, 2014

Related U.S. Application Data

(60) Provisional application No. 61/792,267, filed on Mar. 15, 2013.

(51) Int. Cl.
| | |
|---|---|
| A61N 5/00 | (2006.01) |
| A61L 2/00 | (2006.01) |
| G05B 1/00 | (2006.01) |
| G01N 21/00 | (2006.01) |
| A61L 9/00 | (2006.01) |
| A61L 2/10 | (2006.01) |
| A61L 2/28 | (2006.01) |

(52) U.S. Cl.
CPC ... *A61L 9/00* (2013.01); *A61L 2/00* (2013.01);
*A61L 2/10* (2013.01); *A61L 2/28* (2013.01);
*A61L 2202/14* (2013.01); *A61L 2202/15*
(2013.01); *A61L 2202/24* (2013.01)

(58) Field of Classification Search
CPC ................................. A61L 2/00; A61L 2/0029
USPC ..................... 422/24, 105; 250/455.11, 492.1
See application file for complete search history.

(56) References Cited

U.S. PATENT DOCUMENTS

| | | |
|---|---|---|
| 3,683,638 A | 8/1972 | Devon |
| 3,936,186 A | 2/1976 | Boland et al. |
| 5,288,647 A | 2/1994 | Zimlich et al. |
| 5,597,597 A | 1/1997 | Newman |
| 5,637,877 A | 6/1997 | Sinofsky |
| 6,433,343 B1 | 8/2002 | Cimino et al. |
| 6,461,569 B1 | 10/2002 | Boudreaux |

(Continued)

FOREIGN PATENT DOCUMENTS

| | | |
|---|---|---|
| DE | 2929805 | 1/1981 |
| GB | 2364622 | 1/2002 |

(Continued)

OTHER PUBLICATIONS

PCT International Search Report and Written Opinion, dated Jun. 30, 2015.

(Continued)

*Primary Examiner* — Monzer R Chorbaji
(74) *Attorney, Agent, or Firm* — B. Craig Killough; Barnwell Whaley Patterson & Helms

(57) ABSTRACT

A disinfector disinfects an object having channels therein, such as an endoscope, by one or more light emitting diodes that emit UV-C radiation. The object, including interior channels of the object, is exposed to emissions of UV-C radiation. One or more light emitting diodes provide UV-C radiation to the interior channels of the object. Operation of the device through the channels is responsive to cumulative levels of radiation received by the sensor(s) associated with the light emitting diode(s).

15 Claims, 7 Drawing Sheets

(56) References Cited

U.S. PATENT DOCUMENTS

| | | |
|---|---|---|
| 6,656,424 B1 | 12/2003 | Deal |
| 6,712,756 B1 | 3/2004 | Kura et al. |
| 6,767,453 B2 | 7/2004 | Lifschitz |
| 6,911,177 B2 | 6/2005 | Deal |
| 7,175,806 B2 | 2/2007 | Deal et al. |
| 7,829,016 B2 | 11/2010 | Deal et al. |
| 8,623,275 B2 | 1/2014 | Deshays |
| 2007/0280852 A1 | 12/2007 | Skubal et al. |
| 2008/0075629 A1 | 3/2008 | Deal et al. |
| 2010/0178196 A1 | 7/2010 | Garner |
| 2011/0305597 A1* | 12/2011 | Farren ............................ 422/24 |
| 2012/0282135 A1 | 11/2012 | Trapani |

FOREIGN PATENT DOCUMENTS

| | | |
|---|---|---|
| JP | 11009546 | 1/1999 |
| WO | 9953966 | 10/1999 |

OTHER PUBLICATIONS

International Search Report dated Aug. 11, 2014 in connection with International Patent Application No. PCT/US2014/030203, 4 pages.

Written Opinion of International Searching Authority dated Aug. 11, 2014 in connection with International Patent Application No. PCT/US2014/030203, 10 pages.

\* cited by examiner

INSTRUMENT DISINFECTOR

BACKGROUND OF THE INVENTION

The nature of bacteria acquired in the health care setting differs significantly from bacteria found in a community setting, primarily in their resistance to antibiotic therapy. Abundant evidence exists, however, that the hospital environment itself contributes to the problem by harboring virulent strains of bacteria, fungi, and viruses, and that many disinfection methods commonly used are ineffective and may actually spread contaminants. These contaminants are present on objects, and in particular, instruments, such as endoscopes. These instruments must be decontaminated between uses.

Multiple needs exist to provide disinfection or decontamination of objects that are not suitable for treatment by an autoclave or similar methods. These include, but are not limited to, the exterior of mail, fruits and certain other food items, medical instruments, food handling devices, and other objects that are contaminated with biological hazards.

Examples of such objects are flexible and rigid endoscopes. Endoscopy is a common procedure in modern medical practices. Endoscopes are used to examine and surgically manipulate the sinus cavities, upper and lower gastrointestinal tracts, lung fields, larynx, and intra-abdominal spaces. These endoscopes may have interior channels or conduits that are difficult to reach and disinfect. Relatively straightforward methods exist to disinfect endoscopes that have simple architecture, such as those that do not have interior channels, although the working life of the endoscopes is lessened by chemical degeneration of the seals. An ongoing problem has been the reliable disinfection of endoscopes that have interior channels. These channels are used to inject liquid irrigants, suction, and to pass flexible instruments such as biopsy forceps. These types of interior chambers have represented a challenge to infection control efforts.

Ultraviolet irradiation, particularly in the C bandwidth (2537 Angstroms), when given in adequate doses is lethal to all known pathogens. Ultraviolet irradiation in the C bandwidth (UV-C) is being used to disinfect water supplies, air duct systems, and recently entire patient care areas. The use of UV-C to disinfect endoscopes has not been accomplished to date primarily because of the unavailability of methods of delivering UV-C radiation to interior channels, the unavailability of methods of measuring cumulative dosing that assure adequate decontamination, and the unavailability of methods of measuring UV-C levels that are delivered to the object to be decontaminated.

Microbes are uniquely vulnerable to the effects of light at wavelengths at or near 2537 Angstroms, due to the resonance of this wavelength with molecular structures. For the purposes of this document, the term UV-C is used for a wavelength of light being utilized for its germicidal properties, this wavelength being in the region of 2537 Angstroms.

Recent advances in light emitting diodes (LEDs) have provided the ability to generate UV-C within endoscope channels with sufficient intensity to decontaminate and/or sterilize such channels. Also, the method of measuring an accumulating total energy delivered has recently been developed relative to area disinfecting methods, and effective dose ranges have been established.

The United States Food and Drug Administration and the United States Center For Disease Control and Prevention define disinfection as the use of a chemical procedure that eliminates virtually all recognized pathogenic microorganisms but not necessarily all microbial forms (e.g., bacterial endospores) on inanimate objects. There are three levels of disinfection: high, intermediate, and low. High-level disinfection kills all organisms, except high levels of bacterial spores, and is effected with a chemical germicide cleared for marketing as a sterilant by the Food and Drug Administration. Intermediate-level disinfection kills mycobacteria, most viruses, and bacteria with a chemical germicide registered as a "tuberculocide" by the Environmental Protection Agency (EPA). Low-level disinfection kills some viruses and bacteria with a chemical germicide registered as a hospital disinfectant by the EPA. For the purposes of this document, "disinfection" includes all three of these levels, although disinfection is not achieved solely by chemical means by the process described herein.

SUMMARY OF THE INVENTION

The present invention is a disinfector that disinfects objects having interior channels, such as an endoscope, by subjecting the objects to closed-loop emissions of UV-C radiation. UV-C sensors measure reflected UV-C radiation from interior surfaces and from the objects themselves. The UV-C sensor information is used to determine when a prescribed dose of UV-C radiation has been applied. UV-C radiation is generated in interior by UV-C emitters such as LEDs or other small emitters that may be transported through channels of objects to be disinfected. These emitters provide illumination to a particular area of an object to be disinfected, and that area continues to be exposed with UV-C radiation until the prescribed dose is applied, which may be measured by a sensor. After the prescribed dose is applied, the cable emitters and the sensor are moved to a new area of the object, and the UV-C disinfection process continues until all areas of the object have been disinfected by exposure to the prescribed dose of the UV-C radiation.

DESCRIPTION OF PREFERRED EMBODIMENTS

The disinfector provides decontamination of medical instruments and other objects, with little or no risk of harm to the instruments or objects during the process. The device uses medium pressure mercury bulbs, other bulbs, LEDs and/or other emitters that produce ultraviolet light in the UV-C range, housed in a vertical chamber to irradiate the exterior of an object, such as a medical instrument.

Figure 2:
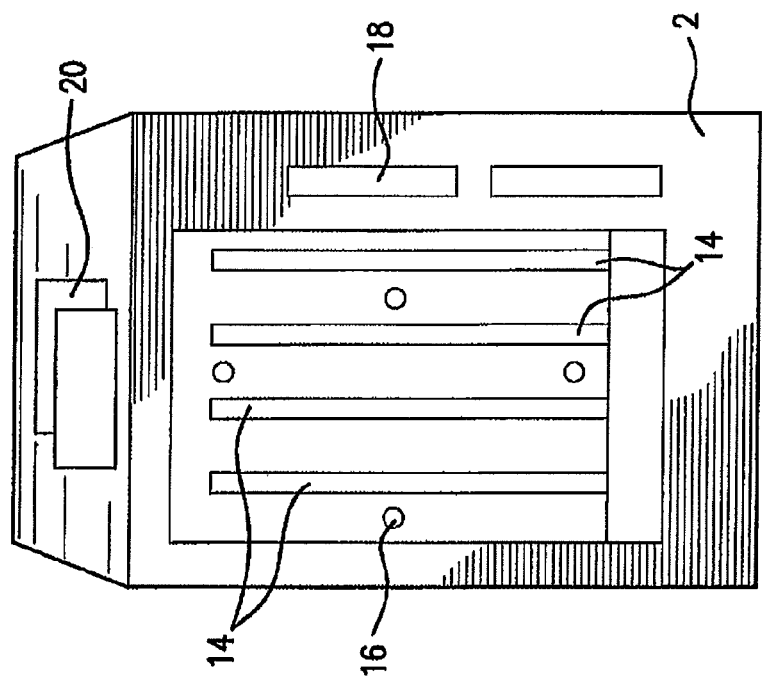
FIG. 2 is a front elevation of the disinfector, showing the internal components of the device.
Figure 1:
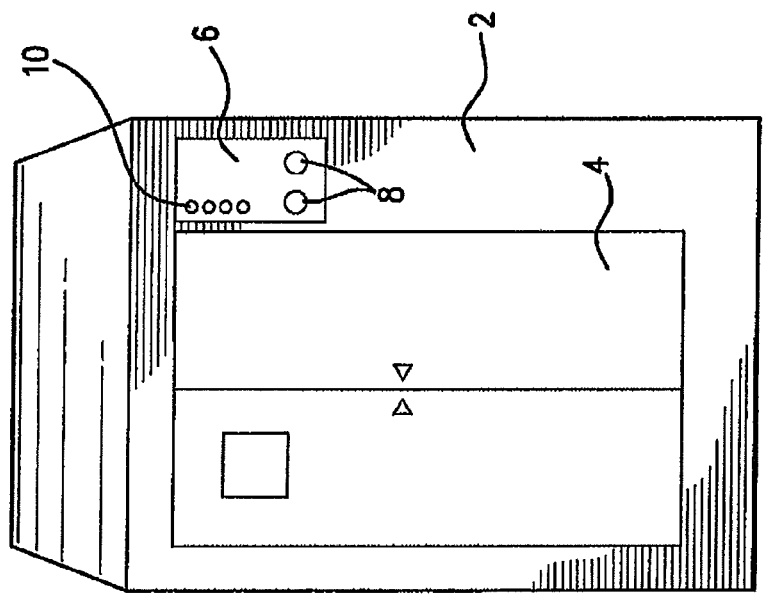
FIG. 1 is a front elevation of the disinfector.

FIG. 1 shows a housing for an embodiment of the device. The housing 2 is preferred to be formed of a metal that is easy to clean, such as stainless steel or powder coated steel. All interior surfaces are preferred to be highly UV-C reflective and configured so as to maximize the dispersion of the reflected UV-C radiation within the sterilization chamber. The reflectivity of the interior surfaces of the housing should not be less than 80%. The device may be capable of floor or wall mounting, according to the user's preference, and according to the overall size of the device.

In this embodiment, the interior is constructed so that dispersion of UV-C radiant flux energy throughout the sterilization chamber is uniform, with both "hot spots" and "shadows" minimized. In this way, the object to be disinfected is treated on all surfaces as uniformly as possible by reflected, if not direct, UV-C radiation.

In the embodiment as shown as FIG. 1, the device has doors 4 that allow access to the interior of the device, and an external control panel 6. The external control panel may have on—off (start—stop) switches 8 and indicator lights 10 that show the status of the process (in-process, complete, error).

Internally, the device has a plurality of UV-C emitters or lamps 14. The UV-C emitters or lamps form a bulb array, with the number and location of the emitters dependent upon the size of the device. The emitters may be placed on any or all interior surfaces. The emitters/bulbs may be protected by fused-quartz glass with high UV-C transmittance.

The device has a plurality of UV-C sensors 16 positioned therein. Multiple sensors may be present on any or all-interior surfaces. In this embodiment, the sensors are located so as to only measure reflected UV-C radiation.

Figure 6:
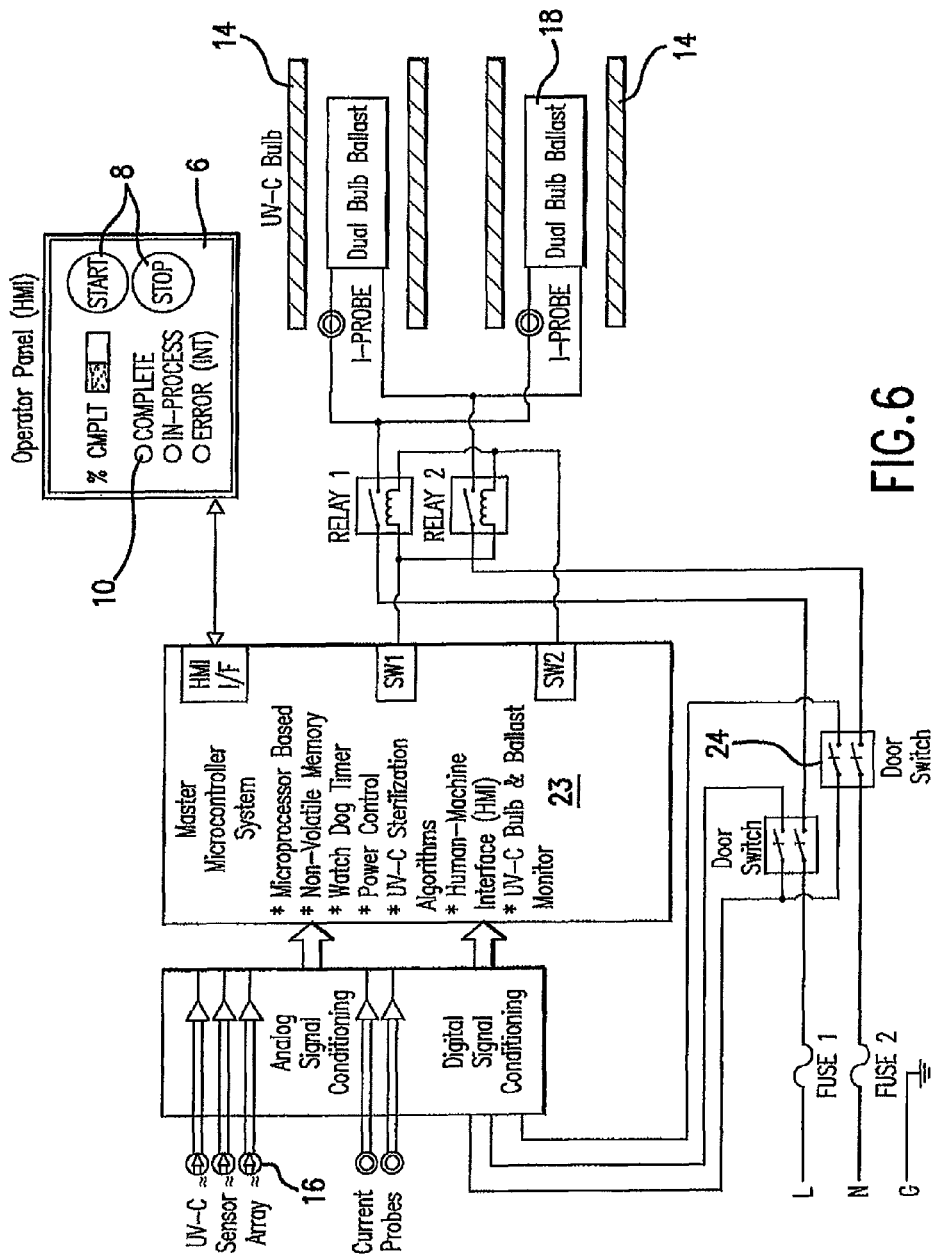
FIG. 6 is a schematic of an embodiment of the C-Band disinfector.
Figure 7:
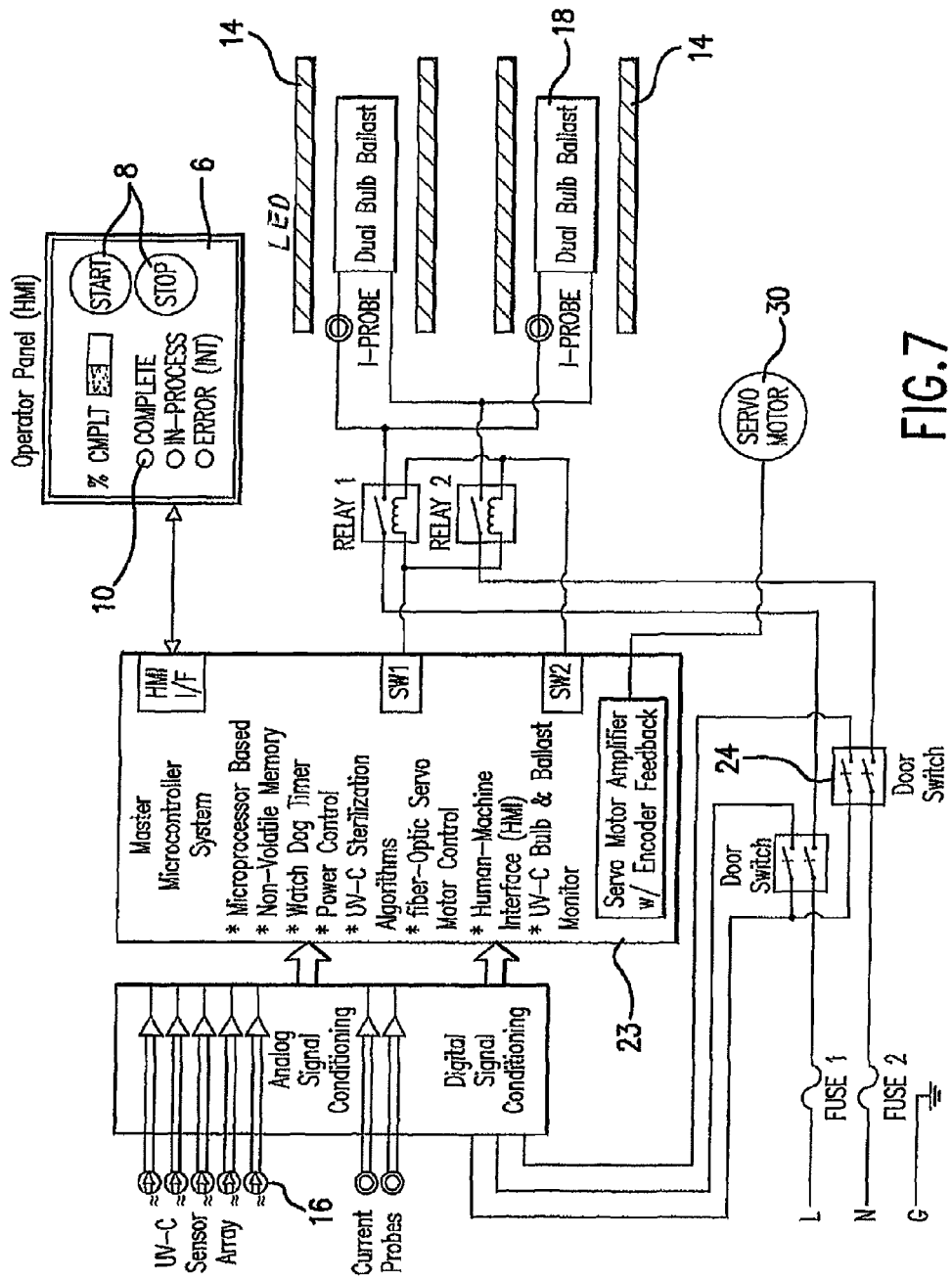
FIG. 7 is a schematic of an additional embodiment of the C-Band disinfector.
Figure 8:
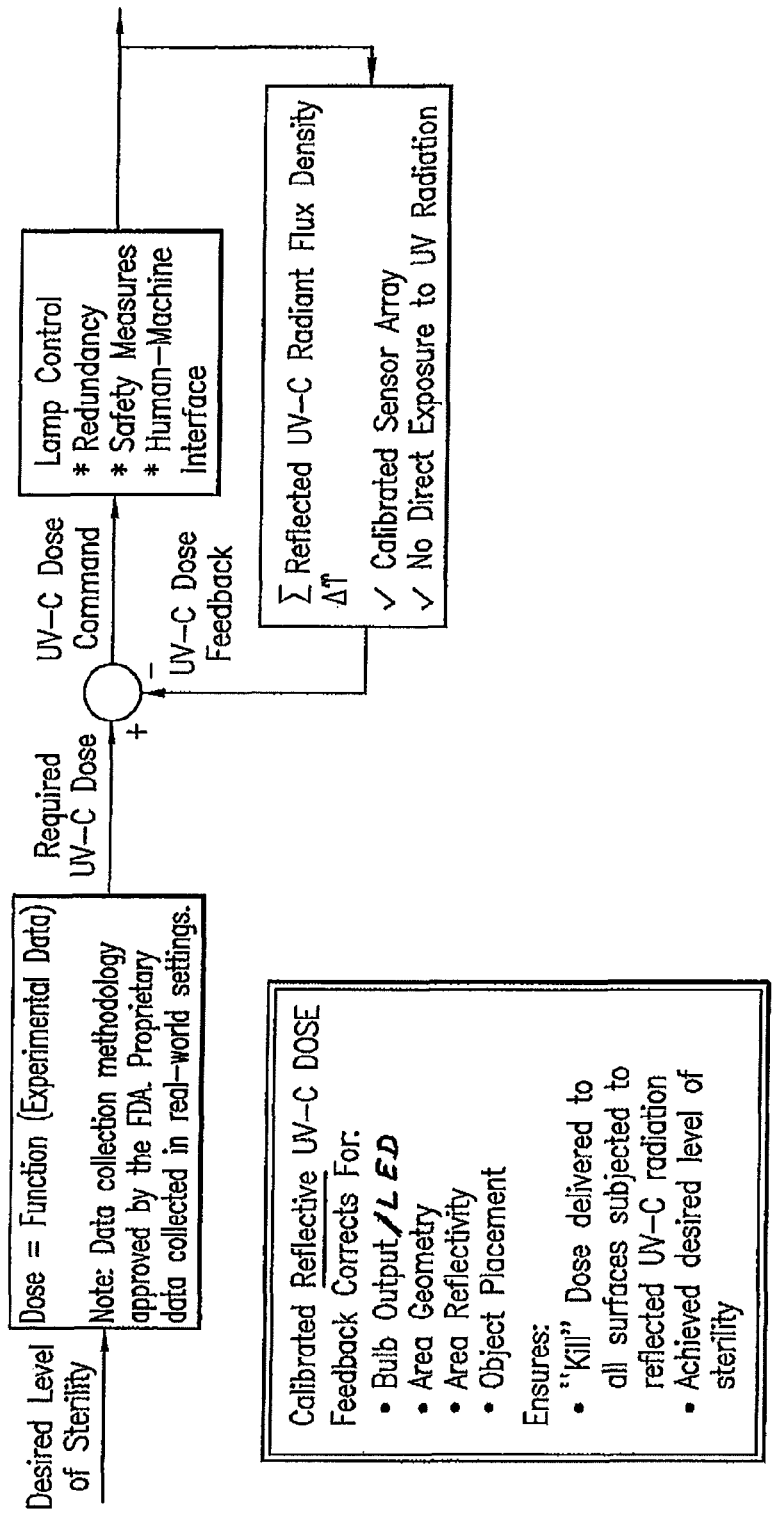
FIG. 8 is a block diagram of operational feature of the C-band disinfector.

The microcontroller system 20 reads the UV-C sensors. Sterilization control algorithms use the measured total, summed dose of UV-C to determine when all surfaces of the object have been exposed to a desired UV-C dosage (FIG. 6; FIG. 7; FIG. 8). Ballasts 18 or other controllers may be provided within the device as required by the UV-C emitter.

Figure 4:
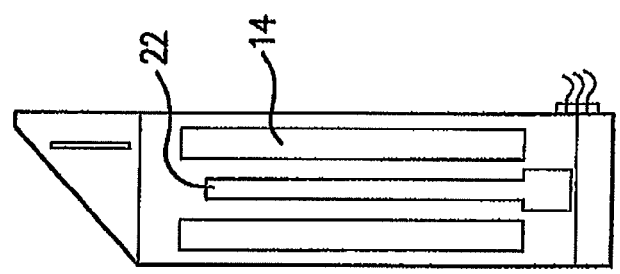
FIG. 4 is a side elevation of an embodiment of the disinfector, showing the device in use.

In use, objects, such as medical devices, which may be endoscopes 22, are placed into the interior of the device. Endoscopes, such as rigid endoscopes, may not have interior channels. Rigid endoscopes that do not have interior channels are demonstrated in FIGS. 3 and 4. These endoscopes are placed into the device, and the doors are closed. The device is actuated by means of an appropriate switch, and UV-C radiation is emitted from the bulb array. Direct and reflected UV-C radiation strikes all exterior surfaces of the endoscopes, and disinfects the endoscopes.

Prior to actuating the device, a desired level of disinfection or UV-C dosage level may be selected. FIG. 6. Each of the sensors receives reflected UV-C radiation, and the cumulative UV-C radiation received by each sensor is transmitted to, and measured by, the microcontroller 23. When the required reflected dosage of UV-C has been received by all of the sensors, the microcontroller terminates power to all of the UV-C bulbs/emitters. By placing sensors at multiple locations within the device, it can be assured that all parts of the device have received, at a minimum, the required dosage. While certain sensors may receive more than the required dosage, the device continues to operate until each of the sensors has achieved at least the minimum programmed dosage. Control algorithms, based on the principle that electromagnetic energy in free air is dissipated in proportion to one divided by the distance from the radiation source squared, insure that the minimum required UV-C dose is transmitted to all external surfaces of the object.

Other features of the device of this embodiment include a door switch 24 that keeps the cabinet from being opened while the device is emitting UV-C radiation. Further, the device is preferred to have a timer algorithm that will override the operation of the device, so that it does not continue to operate for an excessive period of time, even if the minimum dosage is not apparently received by each of the sensors. For example, if a sensor is blocked, or if a sensor is defective, the algorithm will shut the device down so that the device does not run indefinitely. In the event that the microcontroller shuts the device down, an error message is displayed on the control panel.

Other features may include monitoring the current delivered to the light source so as to determine when bulb replacement is required and calibration curves stored within each of the UV-C sensors. Current flowing to the ballast(s) may be monitored, and an hour meter is provided for each of the emitters/bulbs. After the passage of a preset number of hours, the user is notified that the emitter/bulb should be replaced. Also, an algorithm monitors the current, and insures that the current is within certain limits. If not, either a bulb has burned out, or a ballast has failed.

A serial EEPROM is provided on the sensor printed circuit board. The sensor is calibrated to a traceable source, and this calibration curve is stored within the EEPROM. When a new sensor is installed, the control system reads the new calibration curve from the sensor. This feature facilitates subsequent re-calibration and replacement of sensors.

Figure 3:
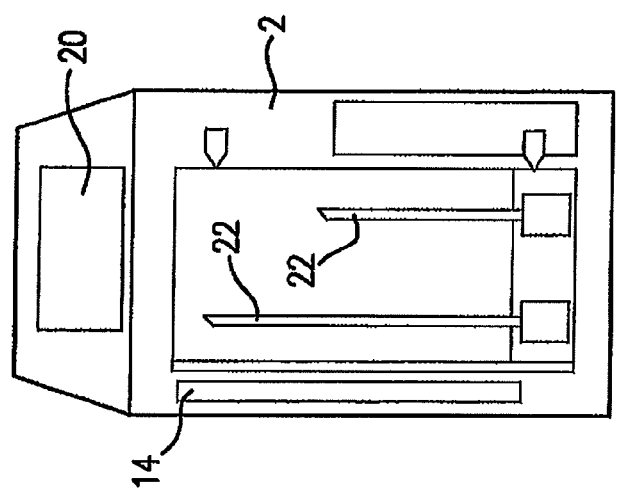
FIG. 3 is a front elevation of an embodiment of the disinfector, showing the device in use.

The embodiment shown in FIG. 3, and in the schematic of FIG. 6, is useful for devices that do not have interior channels. For devices that have interior channels, and due to their structure, will not receive reflected or direct UV-C radiation, an additional embodiment or feature of the device must be provided. In particular, many medical devices, such as flexible endoscopes have an internal channel or conduit that is enclosed, and will not receive reflected or direct UV-C radiation.

Figure 5:
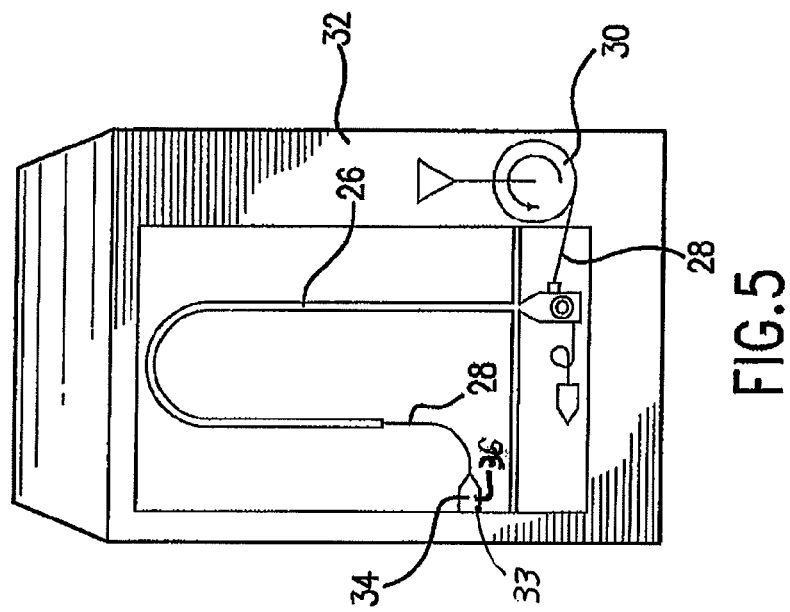
FIG. 5 is an additional embodiment of the C-Band disinfector, showing the device with the velocity controlled cable 28.

For endoscopes 26, or other objects with channels, the embodiment of the device shown in FIG. 5 and FIG. 7 may be used. A cable 28 is present in the cabinet. The cable comprises one or more UV-C emitters, which is preferred to be one or more light emitting diodes (LEDs), and preferably, one or more UV-C sensors 34. After placement of the endoscope into the cabinet 32, and prior to activation of the UV-C emitters, the user inserts the cable 28, through interior channels of the endoscope 26. The sensor is tuned to measure the intensity of, and total dosing of, radiant energy at the appropriate bandwidth. The radiant energy in the form of UV-C radiation is emitted by one or more LEDs located at the end of the cable in one embodiment, with multiple LEDs positioned along the cable in another embodiment. The cable may be formed of an elongated material that will transport the emitter(s) and the sensor through the channel, and provide current to the LED and the sensor, and a signal from the sensor to the device as described herein for controlling withdrawal of the cable.

LED circuitry used with the invention may comprise a printed wiring board, LEDs tuned for C-Band radiation, LED power control circuitry and a high-efficiency AC to DC power supply. Multiple LEDs may present an LED array. The power control circuitry may comprise field effect transistors configured for pulse width modulation.

In one embodiment, UV-C radiation received by the sensor(s) is read by the microcontroller system, which controls the rate of withdrawal of the cable from the endoscope channel with a velocity-controlled withdrawal device 30. The rate of withdrawal is determined by the UV-C radiation dosage received by the sensor(s). The combination of using LEDs to generate UV-C within endoscope channels (or other similar devices with interior channels) and sensor(s) to measure and confirm delivery of a germicidal dose of UV-C represents a novel approach to the sterilization of channeled instruments and endoscopes.

In one embodiment, a UV-C emitting LED 33 and a sensor 34 are positioned at the end of the cable 28. A barrier that does not permit UV-C radiation to pass through may separate the LED from the sensor so that the sensor receives reflected radiation but does not receive direct UV-C radiation. The structure and arrangement of the LED and the sensor may otherwise be such that the sensor does not receive directly UV-C radiation. UV-C radiation received by the sensors is read by the microcontroller system, which controls the rate of withdrawal of the cable from the endoscope channel with a velocity-controlled withdrawal device 30. The rate of withdrawal of the cable and the associated LED is determined by the UV-C radiation dosage received by the sensor. In another embodiment, multiple LEDs are positioned at the end of the cable, if necessary to create the required UV-C dosage, although only one sensor is associated with multiple LEDs in that embodiment.

Figure 10:
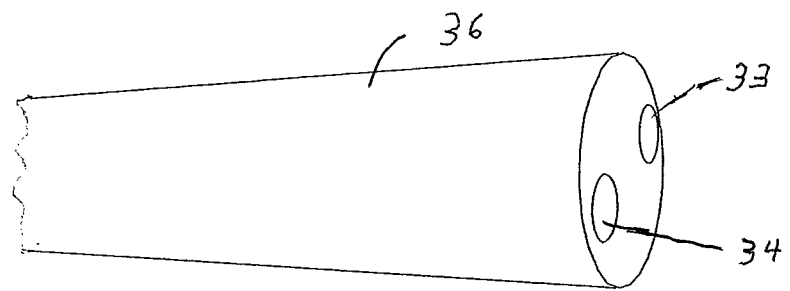
FIG. 10 shows an embodiment of a UV-C emitting LED and a sensor for disinfecting channels.

FIG. 10 shows an exemplary embodiment of a UV-C emitting LED 33 and a sensor 34 located in a terminal housing 36. The terminal housing is positioned at the end of the cable 28. The sensor is recessed in the terminal housing so that the sensor receives reflected radiation, but does not receive direct UV-C radiation from the UV-C emitting LED that is positioned adjacent to the sensor. UV-C radiation received by the sensor 34 is read by the microcontroller system, which controls the rate of withdrawal of the terminal housing and attached cable from the endoscope channel with the velocity-controlled withdrawal device 30.

Alternatively, sensors and the emitters/radiant source, such as LEDs, may be spaced in sufficient density along the length of the cable to allow the treatment of the interior channels without withdrawal of the cable until after the treatment is complete. In one embodiment, multiple UV-C emitting LEDs are spaced apart along the cable. One sensor is associated with each LED, with each LED and sensor pair positioned in a close physical relationship of less than 1 cm. apart. The LED and sensor are structured and arranged on the cable preferably so that the sensor receives reflected, and not direct, radiation.

LEDs that are connected to a cable may be used in combination with fiber optic. For example, fiber optic may be suitable for disinfecting very small channels, while LEDs may be preferable in larger channels. The size of the channel and the material that forms the channel impacts the properties of the emitter that is selected. LEDs may be larger and capable of providing more energy than fiber optic. The sensor that is local to the emitter will also be sized appropriately to the channel.

The cable to which the emitter is attached for positioning the emitter through the channel may also be used to cool the UV-C emitter. For example, the cable may comprise a lumen through which cool air is transmitted to cool a UV-C emitter such as an LED. The cable may comprise conductive materials, which may be metal, such as copper, to conduct heat. The conductive material may also conduct current for powering the emitter, which may be one or more LEDs.

In the case of medical devices that transmit visible light during use, such as those using liquid-filled chambers for light transmission, UV-C may be transmitted through the existing light transmission channels. Leakage or transmission of UV-C into the interior working channels may be measured with a sensor array that is inserted into the working channels, assuring adequate UV-C dosing.

The chamber 32 in which the scopes or other devices are positioned for decontamination is preferred to be constructed of, or coated with, a material that reflects UV-C. As described above, UV-C sensors inside the chamber measure the cumulative dosage, and the sensors send data to a microprocessor that activates and deactivates the UV-C emitters, assuring adequate UV-C dosing to the exterior of the endoscopes. The emitters illuminating the interior of the chamber and the exterior of the endoscopes are deactivated when a desired disinfecting dosage of UV-C has been measured within the chamber. Preferable, simultaneously with activation of the emitters, UV-C radiation is emission at the cable is activated as described herein. After an appropriate delay to allow a steady-state output, the microprocessor calculates the rate of withdrawal of the cable needed to allow for adequate dosing of the channel being treated. The controlled withdrawal device begins to extract the cable at the calculated rate. The rate of withdrawal and thus the total exposure of the channel to UV-C is adjusted according to the intensity of the light measured by the sensors.

Alternatively, the cable may contain multiple emitters, such as multiple LEDs, and multiple sensors to accomplish measured decontamination. As the cable is withdrawn it emits lethal doses of UV-C to the interior channels of the medical instrument. Alternatively, the cable may contain multiple emitters, such as multiple LEDs, and multiple sensors to accomplish measured decontamination, allowing complete treatment of the channel or a significant length of the channel, while the cable is static within the channel during treatment.

The controlled withdrawal device may comprise a geared velocity controlled motor connected to a rubberized soft pulley system. The controlled withdrawal device is designed to pull the cable from the disinfection chamber at a reproducible and controlled speed without damaging the cables. The cable is fed into a coiling chamber located above the light source. The rate of withdrawal of the cable is controlled by the microprocessor and is dependent on the intensity of UV-C measured by the cable output sensor.

Figure 9:
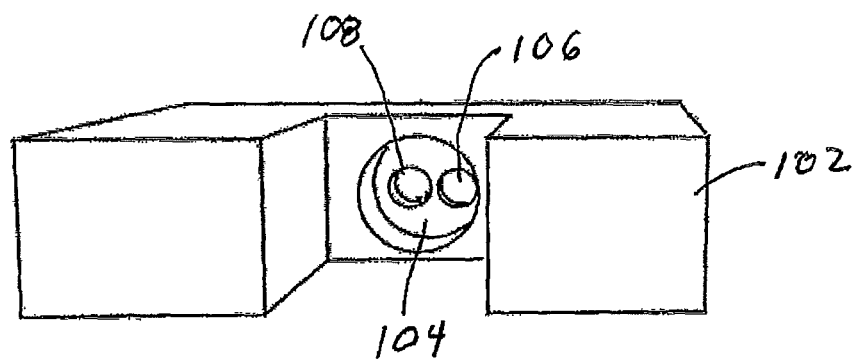
FIG. 9 is an attachment useful in disinfecting channels in devices that have chambers, such as liquid filled chambers, that are capable of transmitting UV-C radiation.

In one embodiment, one or more sensors are recessed into the device 102 depicted in FIG. 9. One end of a channel of a medical device that will transmit UV-C radiation, such as a distal end of scope (the part that goes into the patient) is inserted into the larger recess 104. One or more sensor(s) 106 are positioned inside of the smaller recesses 108. The sensor (s) read UV-C radiation that is transmitted through the channel. The channel may be a liquid filled channel or other that channel that conducts UV-C radiation. It is preferred that radiation is emitted from the channel along the length of the channel on the interior of the medical device, such as an endoscope, so as to disinfect the length of the channel of the medical device. A UV-C generating device is at an opposite end of the channel from the sensor(s). UV-C radiation is generated through the channel, and is received by the sensor (s). The cumulative dosage received by the sensor(s) is measured, and UV-C transmission is terminated upon receipt of the required UV-C dosage by the sensor(s).

The device disinfects the exterior and interior of the endoscope or other object to be treated. Unlike prior wet disinfection devices, this device produces no hazardous wastes or byproducts, does not chemically degrade the endoscope seals, and is estimated to accomplish the task in less time. An additional benefit is that the endoscope or other instruments may be pre-packaged in a material that transmits sufficient amounts of UV-C to allow treatment to occur with the device located within the packaging or container. This allows the endoscope or device to be removed from the disinfector and stored in a manner that maintains sterility.

The device may be used to disinfect other objects having crevices or channels. The emitters and sensors or similar material may be used to direct the UV-C radiation into crevices and channels and destroy pathogens that lurk there.

The endoscopes to be disinfected should be washed of obvious contaminates prior to use with clean water and one or more appropriate cleaning agents. Endoscopes, or other objects to be disinfected, that do not have channels may be treated without use of the cable withdrawal embodiment.

Some objects are sensitive to degradation by UV-C radiation. These objects, or the relevant portion thereof, may be treated or coated with a UV blocking agent for protection from UV-C radiation. Specifically, some fiber-optic cables degrade when exposed to UV-C, and UV-C blocking is desirable. UV protection, as is commonly placed on optical lenses, such as sunglasses or reading glasses, reduces UV-C degradation.

Data is available regarding the levels of UV-C necessary to disinfect against a wide range of organisms including *bacillus* anthrax, *staphylococcal* species, *pseudomonal* species, and *e. coli* species. Previously published data related solely to levels used to kill bacterial species in wet solution. The inventors have found that wet bacteria require less UV-C energy to deactivate than do bacteria in a dry state such as are found on contaminated objects. This data is critical to the use of UV-C to achieve the goals of disinfection or decontamination.

What is claimed is:

1. A device for disinfecting an object having an interior channel, comprising:
   a cable connected to a velocity controlled motor;
   a light emitting diode that emits UV-C radiation positioned near an end of the cable;
   a sensor associated with the light emitting diode and constructed and arranged to not receive a material amount of direct UV-C radiation from the light emitting diode;
   a device for measuring a dosage of UV-C radiation received by the sensor; and
   a controller for controlling a velocity of the velocity controlled motor and attached cable and for controlling a rate of progression of the light emitting diode through the interior channel of the object in response to a UV-C radiation dosage received by the sensor.

2. The device for disinfecting an object having an interior channel as described in claim 1, the device for disinfecting an object having an interior channel further comprising a plurality of light emitting diodes spaced apart along a length of the cable, and having a sensor positioned adjacent to each the light emitting diodes, wherein the cable is withdrawn from the interior channel of the object by the velocity controlled motor in response to the UV-C radiation dosage received by each of the sensors.

3. The device for disinfecting an object having an interior channel as described in claim 1, wherein the light emitting diode is separated from the sensor and the end of the cable is constructed and arranged so that UV-C radiation is not directly received by the sensor from the light emitting diode.

4. The device for disinfecting an object having an interior channel as described in claim 1, the device for disinfecting an object having an interior channel further comprising a housing, said housing comprising a plurality of UV-C radiation sources in an interior thereof, and a plurality of UV-C sensors in an interior thereof, said housing further comprising UV-C reflective interior surfaces, wherein at least one of said UV-C sensors is constructed and arranged to receive UV-C radiation reflected from at least a portion of said UV-C reflective interior surfaces; a device for measuring a cumulative dosage of UV-C radiation received by each of said UV-C sensors, and for terminating an emission of UV-C radiation by said UV-C radiation sources upon each of said UV-C sensors receiving a desired cumulative dosage of UV-C radiation, wherein at least one of the UV-C radiation sources is a light emitting diode.

5. The device for disinfecting an object having an interior channel as described in claim 1, further comprising a terminal housing positioned at the end of the cable, wherein the light emitting diode and the sensor are positioned in the terminal housing relative to each other so that UV-C radiation is not directly received by the sensor from the light emitting diode.

6. A process of disinfecting an interior channel of an object, comprising the steps of: progressively exposing the interior channel of the object to UV-C radiation emitted from a light emitting diode that transmits UV-C radiation by progressively transporting said light emitting diode and a sensor associated with the light emitting diode through the interior channel of the object;
   measuring a dosage of UV-C radiation received by the sensor; and
   adjusting a rate of progression of the light emitting diode through the interior channel of the object in response to a UV-C radiation dosage received by the sensor.

7. The process of disinfecting an object as described in claim 6, wherein the light emitting diode that transmits UV-C radiation and the sensor are positioned near an end of a cable that is progressively transported though the interior channel of the object.

8. The process of disinfecting an object as described in claim 6, wherein the light emitting diode that transmits UV-C radiation and the sensor are positioned near an end of a cable that is progressively transported though the interior channel of the object, wherein the light emitting diode is separated from the sensor and UV-C radiation is not directly received by the sensor from the light emitting diode.

9. The process of disinfecting an object as described in claim 6, further comprising the step of exposing a UV-C conductive interior channel of the object to UV-C radiation emitted from a UV-C radiation source and transmitting UV-C radiation through the UV-C conductive interior channel, wherein a sensor is positioned at an opposite end of the UV-C conductive interior channel to receive UV-C radiation transmitted through the UV-C conductive interior channel;
   measuring a cumulative dosage of UV-C radiation received by the sensor; and
   terminating transmission of UV-C radiation when the desired cumulative dosage of UV-C radiation has been received by the sensor.

10. The process of disinfecting an object as described in claim 6, wherein a plurality of light emitting diodes are spaced apart along a length of the interior channel of the object, wherein the plurality of light emitting diodes is withdrawn from the interior channel of the object in response to a UV-C radiation dosage received by the sensor.

11. The process of disinfecting an object as described in claim 6, placing the object to be disinfected in a housing, said housing comprising a plurality of UV-C radiation sources in an interior thereof, and a plurality of UV-C sensors in an interior thereof, said housing further comprising UV-C reflective interior surfaces, wherein said object is spaced apart from said UV-C radiation sources and said UV-C sensors; directing UV-C radiation from said UV-C radiation sources toward said object and toward said UV-C reflective interior surfaces, wherein said UV-C reflective interior surfaces reflect said UV-C radiation, and wherein at least one of said UV-C sensors receives UV-C radiation reflected from at least a portion of said UV-C reflective interior surfaces; measuring a cumulative dosage of UV-C radiation received by each of said UV-C sensors, and upon each of said UV-C sensors receiving a desired cumulative dosage of UV-C radiation, terminating an emission of UV-C radiation by said UV-C radiation sources.

12. The process of disinfecting an object as described in claim 6, wherein at least one of the UV-C radiation sources is a light emitting diode.

13. The process of disinfecting an object as described in claim 6, wherein a plurality of light emitting diodes are spaced apart along a length of the interior channel of the object, wherein the plurality of light emitting diodes is withdrawn from the interior channel of the object in response to a UV-C radiation dosage received by the sensor, and having a sensor positioned adjacent to each the light emitting diodes.

14. The process of disinfecting an object as described in claim 6, wherein said object is a medical instrument.

15. The process of disinfecting an object as described in claim 6, wherein said object is an endoscope.

* * * * *